(12) United States Patent
Sasmaz et al.

(10) Patent No.: US 11,697,625 B2
(45) Date of Patent: Jul. 11, 2023

(54) DIRECT SYNTHESIS OF LIGHT OLEFINS FROM CARBON DIOXIDE USING YTTRIA-STABILIZED ZIRCONIA SUPPORT

(71) Applicant: THE REGENTS OF THE UNIVERSITY OF CALIFORNIA, Oakland, CA (US)

(72) Inventors: Erdem Sasmaz, Irvine, CA (US); Sunkyu Kim, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 17/452,641

(22) Filed: Oct. 28, 2021

(65) Prior Publication Data
US 2022/0135495 A1  May 5, 2022

Related U.S. Application Data

(60) Provisional application No. 63/107,146, filed on Oct. 29, 2020.

(51) Int. Cl.
| | | |
|---|---|---|
| *C07C 1/12* | (2006.01) | |
| *B01J 23/08* | (2006.01) | |
| *B01J 21/06* | (2006.01) | |
| *B01J 29/85* | (2006.01) | |

(52) U.S. Cl.
CPC .............. *C07C 1/12* (2013.01); *B01J 21/066* (2013.01); *B01J 23/08* (2013.01); *B01J 29/85* (2013.01); *C07C 2521/06* (2013.01); *C07C 2523/08* (2013.01); *C07C 2529/85* (2013.01)

(58) Field of Classification Search
CPC . B01J 29/088; B01J 29/85; B01J 23/08; B01J 21/066; C07C 1/12; C07C 2521/06; C07C 2523/08; C07C 2529/85; C07C 11/04; C07C 11/06; C07C 11/08
See application file for complete search history.

(56) References Cited

PUBLICATIONS

Gao et al., direct production of lower olefins from carbon dioxide conversion via bifunctional catalysis, (ACS Catalysis 2018, 8. 571-578).*
Li et al., carbon dioxide hydrogenation to light olefins over ZnO—Y2O3 and SAPO-34 bifunctional catalysts, (Catalysis Communication 129 (2019)105711.*

* cited by examiner

*Primary Examiner* — Jafar F Parsa
(74) *Attorney, Agent, or Firm* — Nguyen Tarbet LLC

(57) ABSTRACT

The present invention features a direct synthesis of light olefins through the hydrogenation of carbon dioxide. $In_2O_3$ supported on cubic phase yttria-stabilized zirconia is used as a catalyst and is mixed with a molecular sieve to perform the hydrogenation. The cubic crystal structure of the yttria-stabilized zirconium dioxide is an excellent support for indium oxide particles and prevents their deactivation during $CO_2$ hydrogenation. This direct synthesis route promotes a stable and efficient method for producing light olefins.

7 Claims, 3 Drawing Sheets

DIRECT SYNTHESIS OF LIGHT OLEFINS FROM CARBON DIOXIDE USING YTTRIA-STABILIZED ZIRCONIA SUPPORT

CROSS-REFERENCES TO RELATED APPLICATIONS

This application is a non-provisional and claims benefit of U.S. Provisional Application No. 63/107,146, filed Oct. 29, 2020, the specification(s) of which is/are incorporated herein in their entirety by reference.

BACKGROUND OF THE INVENTION

Light olefins (ethylene, propylene, and butylene ($C_2^=$-$C_4^=$)) are key building blocks of polymers, solvents, and drugs, and are produced through cracking of naphtha and dehydrogenation of light paraffins. The use of carbon dioxide ($CO_2$) as a feedstock for the production of light olefins is of interest and can promote sustainable activation of $CO_2$. In one route, $CO_2$ hydrogenation to light olefins can occur through reverse water-gas shift reaction (RWGS) ($CO_2$+$H_2 \leftrightarrows CO+H_2O$, $\Delta H°=42.1$ kJ/mol) followed by chain propagation through Fischer-Tropsch (FT) synthesis (CO+$2H_2 \leftrightarrows$—($CH_2$)—+$H_2O$) on iron or cobalt-based catalysts. However, by this route undesired methane ($CH_4$) can be produced in yields up to 30%, which makes it infeasible.

Alternatively, direct synthesis of light olefins from $CO_2$ is possible through a methanol intermediate ($CO_2$+$3H_2 \leftrightarrows CH_3OH+H_2O$, $\Delta H°=-49.4$ kJ/mol) generated on the copper (Cu)- or indium (In)-based catalysts followed by the methanol-to-olefin (MTO) reaction ($nCH_3OH \leftrightarrows C_nH_{2n}$+$nH_2O$) on molecular sieves such as ZSM-5 and SAPO-34. This route can be accomplished by using bifunctional catalysts, in which metal oxides and molecular sieves are combined together in a single reactor. This direct and single-step route promotes consumption of the intermediate species, shifts the reaction to the product gases, and selectively produces more light olefins compared to the FT process.

However, a major challenge exists for the methanol ($CH_3OH$) mediated route as the MTO reaction is thermodynamically favorable at high reaction temperatures (400-500° C.), whereas $CO_2$ hydrogenation to methanol occurs at lower temperatures (250-325° C.). Any reaction temperature selected above 300° C. will promote the endothermic RWGS reaction leading to high selectivity for undesired CO.

Cu-, In-, and zinc (Zn)-based catalysts have been studied for $CO_2$ hydrogenation to light olefins by the direct route. Cu- and Zn-based catalysts suffer from RWGS and deactivation due to phase segregation or sintering. However, In-based catalysts show high selectivity for methanol and excellent stability due to the defective oxygen vacancy sites and the active indium oxide ($In_2O_3$) phase. Several metal oxide supports have been examined to stabilize the active $In_2O_3$ phase and maintain high activity for methanol synthesis from $CO_2$. Among them, zirconium oxide ($ZrO_2$) supports are beneficial for methanol synthesis. This may be due to the high electronic interaction and relevance of the $In_2O_3$—$ZrO_2$ interface.

Recent studies for the direct light olefin synthesis from $CO_2$ have been guided by the advancements achieved on $In_2O_3/ZrO_2$ catalysts for methanol synthesis. $In_2O_3/ZrO_2$ physically mixed with SAPO-34 can show $C_2^=$-$C_4^=$ selectivity up to 80% with $CO_2$ conversion of 35% at 400° C. and 3 MPa. It is important to note that the reported light olefin selectivity in these studies is high because the undesired CO amount has been excluded while calculating the light olefin selectivity. Despite their good activity, In-based catalysts can show a decrease in the light olefin selectivity as a function of time as the $In_2O_3$ phase can be reduced during the reaction, which promotes the undesired RWGS rather than generating light olefins. Hence, there is a need for novel catalysts with strong $In_2O_3$-support interaction.

BRIEF SUMMARY OF THE INVENTION

The present invention relates to catalysis, more specifically, catalysis for converting carbon dioxide to light olefins. It is an objective of the present invention to provide methods that allow for the catalytic activation of $CO_2$ to light olefins, as specified in the independent claims. Embodiments of the invention are given in the dependent claims. Embodiments of the present invention can be freely combined with each other if they are not mutually exclusive.

In some aspects, the present invention features a method of synthesizing a light olefin. The method may comprise precipitating a catalyst onto zirconia to produce a supported catalyst, adding the supported catalyst into a reactor, mixing a molecular sieve with the supported catalyst in the reactor, introducing hydrogen gas and carbon dioxide gas into the reactor, and heating the reactor. Without wishing to limit the invention to a particular theory or mechanism, a hydrogenation reaction occurs between the hydrogen gas and carbon dioxide gas to synthesize the light olefin. In some embodiments, the synthesized light olefin is ethylene, propylene or butylene.

In some embodiments, the catalyst is an indium-based catalyst. For example, the catalyst may be indium oxide, metallic indium, an indium alloy, an indium single atom catalyst, or an indium single atom alloy. In some embodiments, the supported catalyst may comprise at least 10 wt % of indium.

In other embodiments, the zirconia is cubic phase yttria-stabilized zirconia. Without wishing to limit the invention to a particular theory or mechanism, the cubic phase yttria-stabilized zirconia prevents deactivation of the indium-based catalyst during hydrogenation. In some other embodiments, the molecular sieve is SAPO-34 zeolite, SAPO-5 zeolite, ZSM-5, zeolite beta, or zeolite Y.

In some embodiments, the reactor can be heated to a temperature of about 250° C.-550° C. In other embodiments, the reactor can be maintained at a pressure of about 10 bar-100 bar. In some embodiments, the ratio of hydrogen gas to carbon dioxide gas is at least 3.

According to other aspects, the present invention provides a catalyst composition for producing light olefins from $CO_2$. The catalyst composition may comprise an indium-based catalyst supported on cubic phase yttria-stabilized zirconia, and molecular sieves. In one embodiment, the indium-based catalyst is indium oxide, metallic indium, an indium alloy, an indium single atom catalyst, or an indium single atom alloy. In another embodiment, the molecular sieve is SAPO-34 zeolite, SAPO-5 zeolite, ZSM-5, zeolite beta, or zeolite Y.

Activation of $CO_2$ to light olefins is a challenging reaction and can be achieved through a methanol intermediate route in a single reactor. In this invention, $In_2O_3$ supported on $ZrO_2$ and zeolite molecular sieves is used as a catalyst to produce light olefins from $CO_2$. The cubic crystal structure of the yttria-stabilized zirconium dioxide (YSZ) is an excellent support for $In_2O_3$ particles and prevents their deactivation during $CO_2$ hydrogenation. When these oxide materials are combined with molecular sieves (SAPO-34), stable and high performance of light olefins production is achieved.

One of the unique and inventive technical features of the present invention is the use of YSZ to support the indium-based catalyst. Without wishing to limit the invention to any theory or mechanism, it is believed that the technical feature of the present invention advantageously provides for the activation of $CO_2$ to directly synthesize light olefins.

None of the presently known prior references or work has the unique inventive technical feature of the present invention. Furthermore, the inventive technical features of the present invention contributed to a surprising result. For example, during a 45 h hydrogenation reaction, the $In_2O_3$/c-YSZ+SAPO-34 catalyst did not deactivate, the CO selectivity remained between 81.6-82.2%, and the light olefins selectivity reached up to 11.8%. By comparison, a conventional catalyst used for the same reaction for 45 h results in deactivation of the catalyst, the light olefins selectivity is 9.7% initially but decreases to 4.2%, and CO selectivity is initially 81.6% and increases up to 91.8%. Furthermore, the light olefins yield using the $In_2O_3$/c-YSZ+SAPO-34 catalyst is almost three times higher than the one observed in the conventional $In_2O_3$/m$ZrO_2$+ SAPO-34 catalyst.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which.

Figure 1:
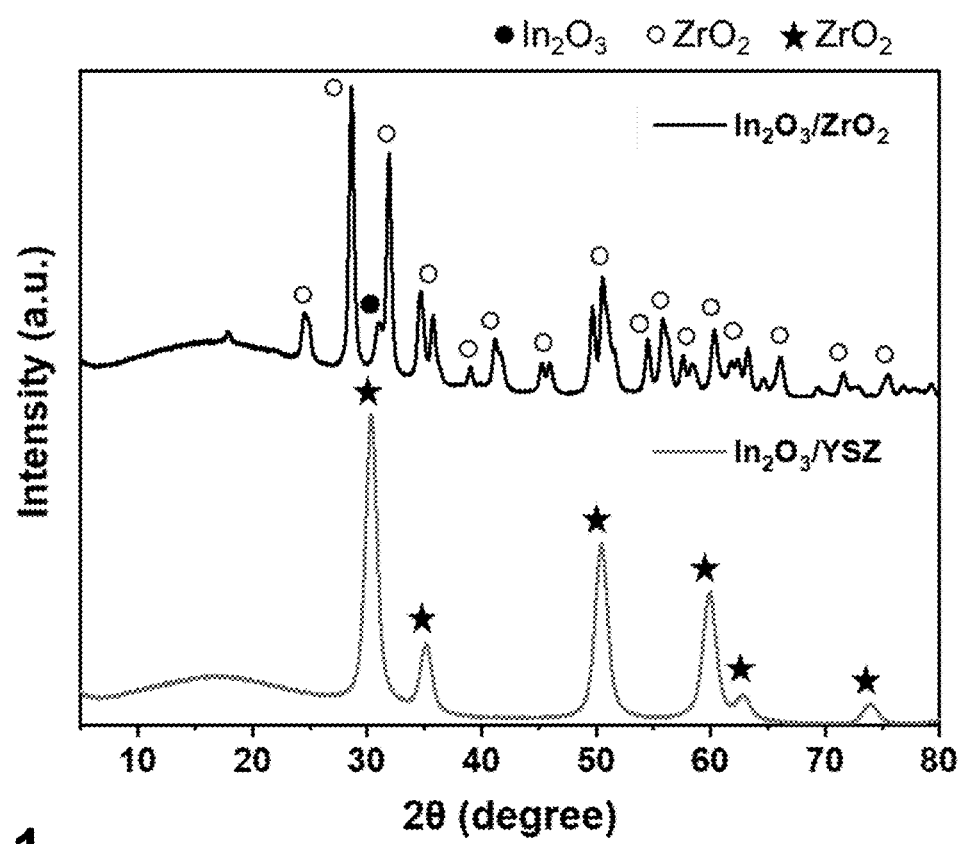
FIG. 1 shows X-ray diffraction (XRD) patterns of the synthesized $In_2O_3$/$ZrO_2$ and $In_2O_3$/YSZ catalysts.

As used herein, the term "light olefin" refers to ethylene, propylene, and butylene ($C_2^=$-$C_4^=$).

As known to one of ordinary skill in the art, the term "cubic phase" when referring to a crystal structure is a crystal phase where the unit cell is in the cubic shape.

As used herein, the term "supported catalyst" refers to active catalysts distributed on a high surface area of a solid.

As used herein, the term "molecular sieve" is a material with micro or meso pores of uniform size.

In some embodiments, the present invention features a method of synthesizing a light olefin from carbon dioxide. The method comprises: 1) precipitating a catalyst onto zirconia to produce a supported catalyst; 2) adding the supported catalyst into a reactor; 3) mixing a molecular sieve with the supported catalyst in the reactor; 4) introducing hydrogen gas and carbon dioxide gas into the reactor; and 5) heating the reactor. A hydrogenation reaction occurs between the hydrogen gas and the carbon dioxide gas to synthesize the light olefin. Non-limiting embodiments of the synthesized light olefin produced by in the present invention include ethylene, propylene or butylene.

In one embodiment, the catalyst is an indium-based catalyst. Non-limiting examples of indium-based catalysts include indium oxide ($In_2O_3$), metallic indium, indium alloys, indium single atom catalysts, or indium single atom alloys. In another embodiment, other metal-based catalysts can be used. Non-limiting examples of other metal-based catalysts include Cu-, Zn-, Cr-, or Fe-based catalysts.

In preferred embodiments, the zirconia is cubic phase yttria-stabilized zirconia. In some embodiments, the supported catalyst may comprise about 1-20 wt % of the indium-based catalysts. For example, the supported catalyst may comprise at least 10 wt % of indium. In other embodiments, the supported catalyst may comprise about 1-10 wt % of indium. In some embodiments, the supported catalyst may comprise about 5-15 wt % of indium. In some other embodiments, the supported catalyst may comprise about 10-20 wt % of indium.

In alternative embodiments, any reducible oxide can be used to support the catalyst. Non-limiting examples of other reducible oxides include $CeO_2$, MnOx, $TiO_2$, $HfO_2$, $Fe_2O_3$, CoOx, VOx, PrOx, or SmOx. In other embodiments, non-limiting examples of the molecular sieves used in the reaction include SAPO-34 zeolite, SAPO-5 zeolite, ZSM-5, zeolite beta, zeolite Y, or a combination thereof.

According to other embodiments, the present invention features a method of synthesizing a light olefin. The method may comprise 1) precipitating an indium-based catalyst onto cubic phase yttria-stabilized zirconia to produce an indium-based supported catalyst; 2) adding the indium-based supported catalyst into a reactor; 3) mixing a molecular sieve with the indium-based supported catalyst in the reactor; 4) introducing a stream of hydrogen gas and a stream of carbon dioxide gas into the reactor; and 5) heating the reactor. A hydrogenation reaction occurs between the hydrogen gas and the carbon dioxide gas to synthesize the light olefin.

Non-limiting examples of indium-based catalysts include indium oxide ($In_2O_3$), metallic indium, indium alloys, indium single atom catalysts, or indium single atom alloys. In other embodiments, other metal-based catalysts can be used. Non-limiting examples of other metal-based catalysts include Cu-, Zn-, Cr-, or Fe-based catalysts. In other embodiments, the molecular sieve is SAPO-34 zeolite, SAPO-5 zeolite, ZSM-5, zeolite beta, or zeolite Y.

In accordance with any of the methods described herein, the reactor can be heated to a temperature ranging from about 250° C. to about 550° C. In other embodiments, the reactor is heated to a temperature of about 250° C.-350° C. In some embodiments, the reactor is heated to a temperature of about 300° C.-400° C. In other embodiments, the reactor is heated to a temperature of about 350° C.-450° C. In some embodiments, the reactor is heated to a temperature of about 400° C.-500° C. In other embodiments, the reactor is heated to a temperature of about 450° C.-550° C.

In accordance with any of the methods described herein, the reactor can be maintained at a pressure ranging from about 10 bar to about 100 bar. In some embodiments, the reactor is maintained at a pressure of about 10-30 bar during the hydrogenation reaction. In other embodiments, the reactor is maintained at a pressure of about 20-40 bar during the hydrogenation reaction. In some embodiments, the reactor is maintained at a pressure of about 30-50 bar during the hydrogenation reaction. In other embodiments, the reactor is maintained at a pressure of about 40-60 bar during the hydrogenation reaction. In some embodiments, the reactor is maintained at a pressure of about 50-70 bar during the hydrogenation reaction. In other embodiments, the reactor is maintained at a pressure of about 60-80 bar during the hydrogenation reaction. In some embodiments, the reactor is maintained at a pressure of about 70-90 bar during the hydrogenation reaction. In other embodiments, the reactor is maintained at a pressure of about 80-100 bar during the hydrogenation reaction.

In accordance with any of the methods described herein, the mole ratio of hydrogen gas to carbon dioxide gas can range from about 2 to 5. In one embodiment, the mole ratio of hydrogen gas to carbon dioxide gas is at least 2. In another embodiment, the mole ratio of hydrogen gas to carbon dioxide gas is at least 3. In some embodiments, the mole ratio of hydrogen gas to carbon dioxide gas is at least 4. In other embodiments, the mole ratio of hydrogen gas to carbon dioxide gas is at least 5.

EXAMPLE

The following is a non-limiting example of the present invention. It is to be understood that said example is not intended to limit the present invention in any way. Equivalents or substitutes are within the scope of the present invention.

$In_2O_3$ supported on cubic phase YSZ and monoclinic $ZrO_2$ are synthesized via an incipient wetness impregnation method. Indium nitrate hydrate is precipitated on the YSZ and $ZrO_2$ supports, leading to 10 wt % of indium on each support. The precipitated $In_2O_3$/YSZ and $In_2O_3$/$ZrO_2$ are then dried and calcined at 500° C. for 4 h.

The synthesized supported $In_2O_3$ catalysts are physically mixed with SAPO-34 zeolite and evaluated for their $CO_2$ hydrogenation activity. FIG. 1 shows XRD patterns of the synthesized $In_2O_3$/$ZrO_2$ and $In_2O_3$/YSZ catalysts. XRD results confirm that $In_2O_3$/$ZrO_2$ has a monoclinic phase of $ZrO_2$ along with $In_2O_3$, whereas $In_2O_3$/YSZ has a cubic phase of $ZrO_2$. The hydrogenation reaction is tested at 400° C. at 30 bar in a feed stream of $H_2$ and $CO_2$ with a $H_2$:$CO_2$ ratio of 3.

Figure 2A:
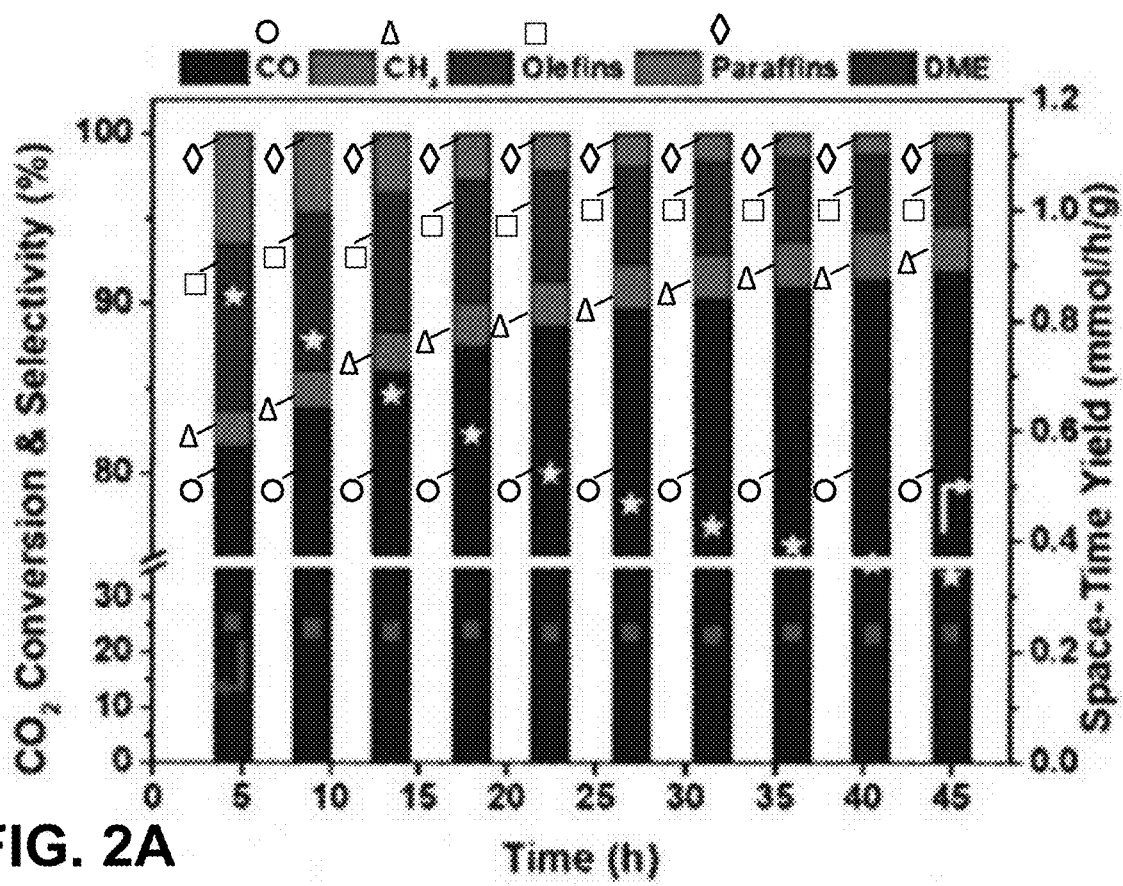
FIGS. 2A-2B show the activity comparison between $In_2O_3$/$ZrO_2$+SAPO-34 and $In_2O_3$/YSZ+SAPO-34.
Figure 2B:
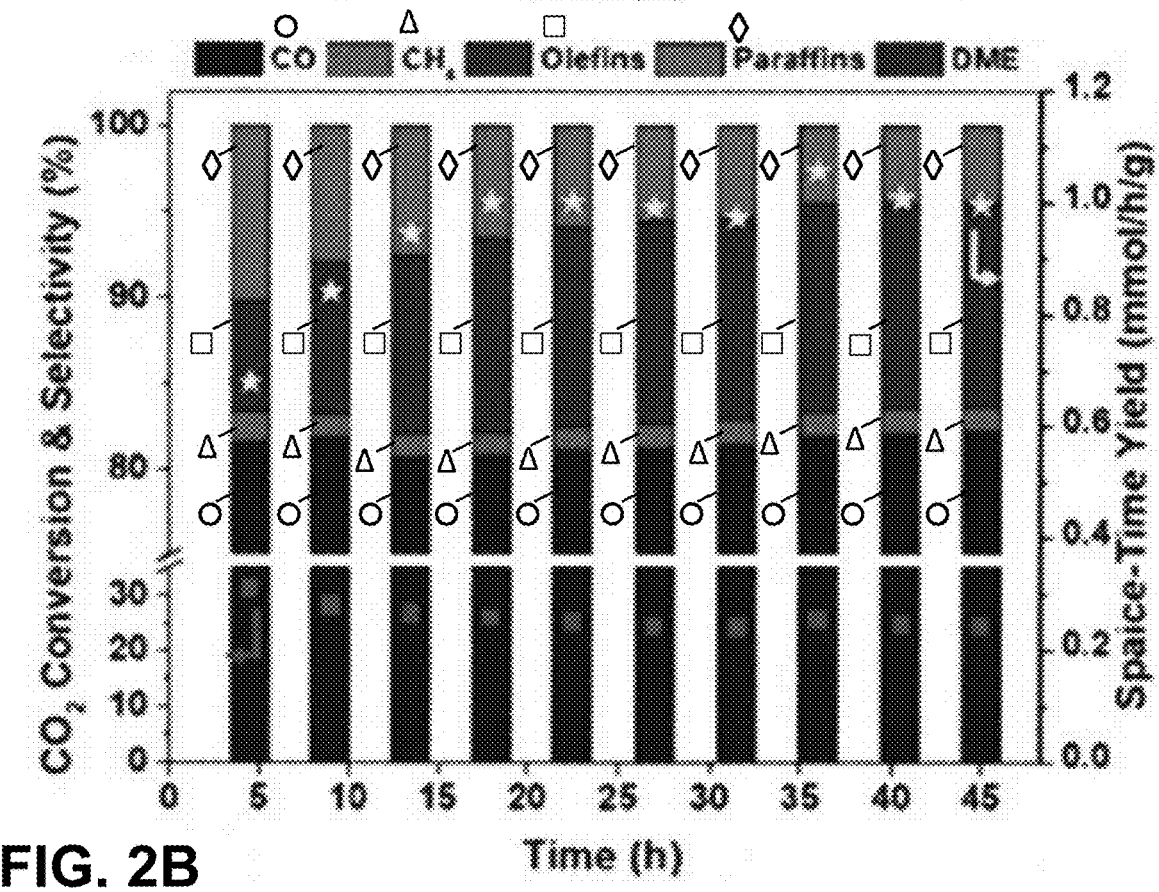

FIGS. 2A-2B show the activity comparison between $In_2O_3$/$ZrO_2$+SAPO-34 and $In_2O_3$/YSZ+SAPO-34. In FIG. 2A, for the conventional $In_2O_3$/$ZrO_2$+SAPO-34, the light olefins selectivity decreases with increasing CO selectivity leading to a low light olefins yield after 45 h of reaction. In FIG. 2B, the $In_2O_3$/YSZ+SAPO-34 shows stable and high light olefins selectivity, leading to a higher light olefins yield during 45 h of reaction.

Figure 3:
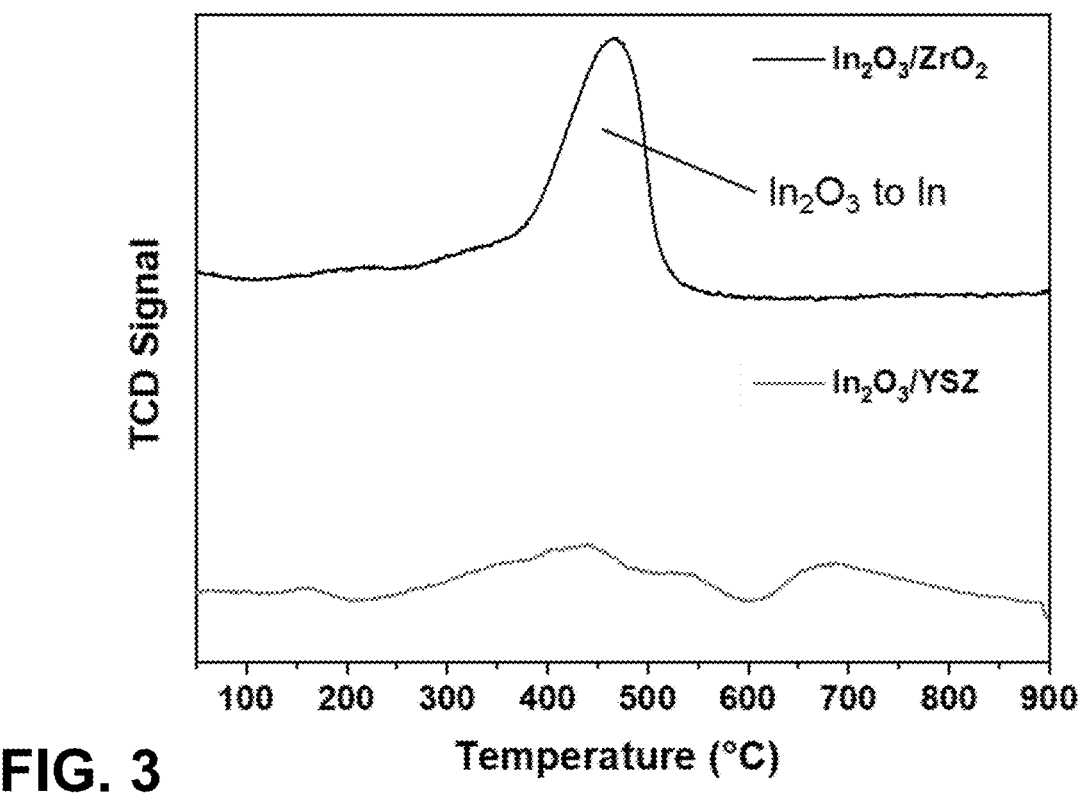
FIG. 3 shows the $H_2$-temperature programmed reduction ($H_2$-TPR) of the synthesized $In_2O_3$/$ZrO_2$ and $In_2O_3$/YSZ catalysts.
Figure 4:
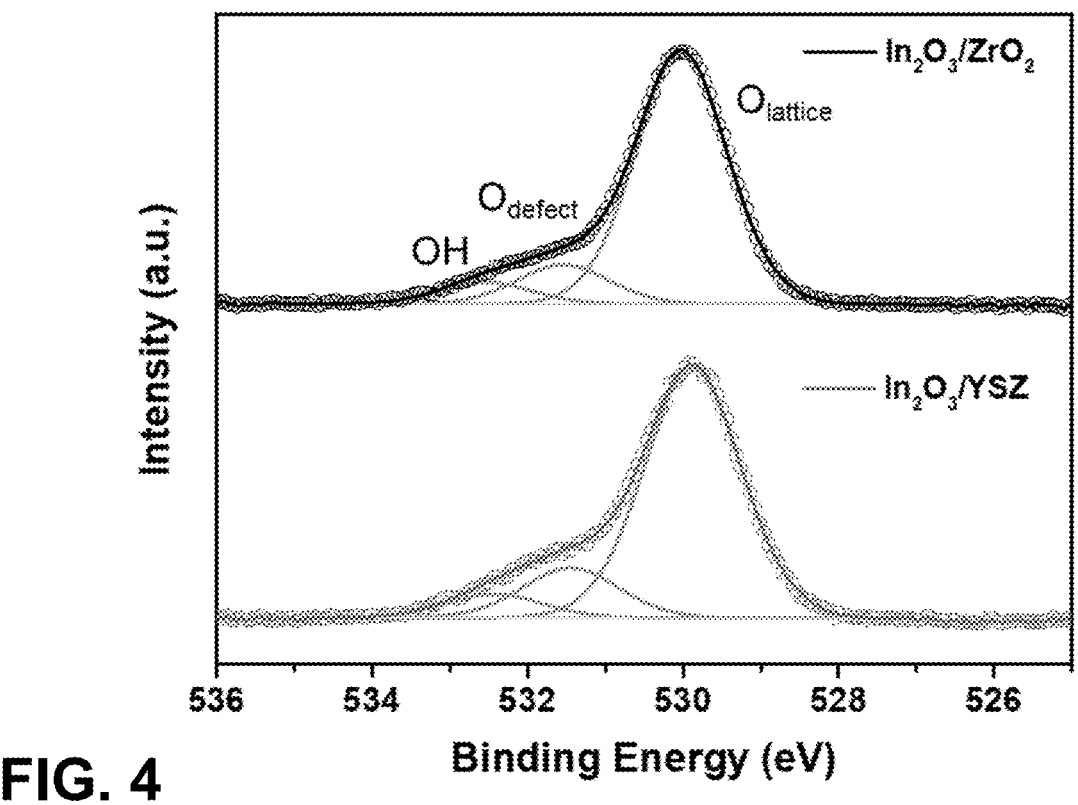
FIG. 4 shows the X-ray photoelectron spectroscopy (XPS) of the synthesized $In_2O_3$/$ZrO_2$ and $In_2O_3$/YSZ catalysts.

FIGS. 3 and 4 show the $H_2$-temperature programmed reduction ($H_2$-TPR) and XPS of the synthesized $In_2O_3$/$ZrO_2$ and $In_2O_3$/YSZ catalysts. In FIG. 3, the strong peak observed at 450° C. in the $In_2O_3$/$ZrO_2$ represents the $In_2O_3$ reduction. In the case of $In_2O_3$/YSZ, the $In_2O_3$ reduction peak is not observed distinctly, indicating that $In_2O_3$/YSZ has a stronger metal-support interaction.

Additionally, O 1 s core level XPS spectra in FIG. 4 shows that the $In_2O_3$/YSZ has a larger oxygen defect concentration (15.4%) than that of $In_2O_3$/$ZrO_2$ (12.6%). The larger oxygen defect concentration on YSZ can increase lattice oxygen mobility which facilitates the movement of oxygen ions and improves the activity and selectivity for light olefins. $CO_2$ hydrogenation is active at the oxygen vacancies of $In_2O_3$ whereas RWGS is active on metallic indium. It is also possible that the conventional $In_2O_3$/$ZrO_2$ catalyst is getting reduced during the reaction leading to a high CO production. However, the $In_2O_3$/YSZ catalyst shows stable activity as it is not reduced due to the stronger interaction between $In_2O_3$ and YSZ.

The conventional $In_2O_3$/$ZrO_2$+SAPO-34 catalyst shows deactivation during $CO_2$ hydrogenation. The initial undesired CO selectivity is 81.6% and increases up to 91.8% after 45 h of reaction. The light olefins selectivity is 9.7% in the beginning of the reaction, but decreases to 4.2% leading to a low light olefins yield of 0.336 mmol/h/g. However, the $In_2O_3$/YSZ+SAPO-34 catalyst does not deactivate during 45 h of reaction. The CO selectivity remains between 81.6-82.2%, and the light olefins selectivity improves and reaches up to 11.8% after 45 h of reaction. The light olefins yield is calculated to be 0.997 mmol/h/g, which is almost three times higher than the one observed in the conventional $In_2O_3$/$ZrO_2$+SAPO-34 catalyst. The $In_2O_3$/YSZ+SAPO-34 catalyst would require less energy to operate while producing higher light olefins selectivity.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

As used herein, the term "about" refers to plus or minus 10% of the referenced number.

What is claimed is:

1. A method of synthesizing a light olefin, the method comprising:
   a. precipitating an indium-based catalyst onto cubic phase yttria-stabilized zirconia (YSZ) to produce a supported indium-based catalyst;
   b. adding the supported indium-based catalyst into a reactor;
   c. mixing a molecular sieve with the supported indium-based catalyst in the reactor;
   d. introducing a stream of hydrogen gas and a stream of carbon dioxide gas into the reactor; and
   e. heating the reactor, wherein a hydrogenation reaction occurs between the hydrogen gas and carbon dioxide gas to synthesize the light olefin;
       wherein the cubic phase YSZ prevents deactivation of the indium-based catalyst during hydrogenation.

2. The method of claim 1, wherein the light olefin is ethylene, propylene, or butylene.

3. The method of claim 1, wherein the indium-based catalyst is indium oxide, metallic indium, an indium alloy, an indium single atom catalyst, or an indium single atom alloy.

4. The method of claim 1, wherein the molecular sieve is SAPO-34 zeolite, SAPO-5 zeolite, ZSM-5, zeolite beta, or zeolite Y.

5. The method of claim 1, wherein the reactor is heated at a temperature of about 250° C.-550° C.

6. The method of claim 1, wherein the reactor is maintained at a pressure of about 10 bar-100 bar.

7. The method of claim 1, wherein the ratio of hydrogen gas to carbon dioxide gas is at least 3.

\* \* \* \* \*